United States Patent
Gao et al.

(10) Patent No.: US 6,531,139 B1
(45) Date of Patent: *Mar. 11, 2003

(54) SELF-EMULSIFYING FORMULATION FOR LIPOPHILIC COMPOUNDS

(75) Inventors: Ping Gao, Portage; Walter Morozowich, Kalamazoo, both of MI (US)

(73) Assignee: Pharmacia & Upjohn Company, Kalamazoo, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/122,926

(22) Filed: Jul. 27, 1998

Related U.S. Application Data

(60) Provisional application No. 60/054,078, filed on Jul. 29, 1997.

(51) Int. Cl.$^7$ .......................... A61K 9/48; A61K 31/44; A61K 31/35
(52) U.S. Cl. .................. 424/400; 424/451; 424/455; 424/456; 514/2; 514/9; 514/169; 514/315; 514/336; 514/456; 514/459; 514/460; 514/557; 514/558; 514/560; 514/573; 514/937; 514/11
(58) Field of Search .................. 424/400, 451, 424/455, 456; 514/2, 9, 169, 459, 460, 557, 558, 560, 937–943, 315, 336, 456, 573

(56) References Cited

U.S. PATENT DOCUMENTS

| | | | |
|---|---|---|---|
| 4,230,702 A | | 10/1980 | Eckert et al. |
| 5,504,068 A | * | 4/1996 | Komiya ..................... 514/11 |
| 5,639,724 A | * | 6/1997 | Cavanak .................... 514/11 |
| 5,645,856 A | * | 7/1997 | Lacy ........................ 424/455 |

FOREIGN PATENT DOCUMENTS

| | | |
|---|---|---|
| EP | 0 267 617 A1 | 5/1988 |
| GB | 2 222 770 A | 3/1990 |
| GB | 2 228 198 A | 8/1990 |
| GB | 2 257 359 B | 10/1996 |
| WO | 94/08603 * | 4/1994 |
| WO | WO95/30670 | 11/1995 |
| WO | WO96/39142 | 12/1996 |
| WO | WO98/22106 | 5/1998 |

* cited by examiner

*Primary Examiner*—Gollamudi S. Kishore
(74) *Attorney, Agent, or Firm*—Lucy X. Yang; Austin W. Zhang; Sidney B. Williams, Jr.

(57) ABSTRACT

The present invention provides a novel pharmaceutical composition based on the use of a particular oil phase which comprises a lipophilic, pharmaceutically active agent, a mixture of diglyceride and monoglyceride in a ratio of from about 9:1 to about 6:4 by weight (diglyceride:monoglyceride) wherein the diglyceride and monoglyceride are mono- or di- unsaturated fatty acid esters of glycerol having sixteen to twenty-two carbon chain length, one or more pharmaceutically acceptable solvents, and one or more pharmaceutically acceptable surfactants. The composition is in a form of self-emulsifying formulation which provides high concentration and high oral bioavailability for lipophilic compounds.

39 Claims, No Drawings

SELF-EMULSIFYING FORMULATION FOR LIPOPHILIC COMPOUNDS

CROSS-REFERENCE TO RELATED APPLICATION

This application claims the benefit of the following provisional application: U.S. Ser. No. 60/054,078, filed Jul. 29, 1997, under 35 USC 119(e)(i).

FIELD OF THE INVENTION

The present invention relates to novel pharmaceutical compositions in a form of a self-emulsifying formulation which provide high concentration and high oral bioavailability for lipophilic, pharmaceutically active agents.

BACKGROUND OF THE INVENTION

It has recently been discovered that certain pyranone compounds inhibit retroviral protease and thus they are useful for treating patients infected with human immunodeficiency virus (HIV) which results in acquired immunodeficiency syndrome (AIDS). In particular, the pyranone compound of formula I has been found to be especially effective as an inhibitor of retroviral protease.

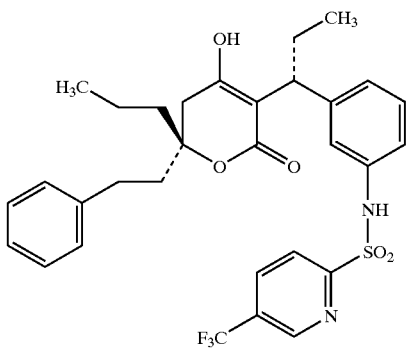

I

However, like many other HIV protease inhibitors, these compounds are characteristically lipophilic and thus poorly water soluble. For example, the compound of formula I has an aqueous solubility about 1 μg/ml in the buffer of pH 6.5 (close to the pH of the intestine), which is considered as extremely poor aqueous solubility and would be expected to provide very low oral bioavailability in the free acid form. It is well known that an active drug substance or therapeutic moiety administered by any route must possess some aqueous solubility for systemic absorption and therapeutic response. Poorly water soluble compounds often exhibit either incomplete or erratic absorption and thus produce a minimal response at desired dosage.

Attempts were made to identify salts of the pyranone compounds in solid forms which could improve aqueous solubility. An overriding defect which has however remained is that the formulations in the form of salt are prone to precipitation of the parent free acid in the gastrointestinal tract and hence are not capable to provide a dosage in the desired high concentration to permit convenient use and yet meet the required criteria in terms of bioavailability.

Recognizing the problems, the present invention is directed toward pharmaceutical compositions in a form of self-emulsifying formulations which provide high concentration and high oral bioavailability for pyranone compounds. In particular it has been discovered that the compositions of the present invention allow the preparation of self-emulsifying formulations containing a pyranone inhibitor of retroviral protease in an exceedingly high concentration up to about 400 mg/g to permit convenient oral administration while at the same time achieving improved bioavailability, which is at least two fold higher than the aqueous suspension of the free acid.

It has also been discovered that the compositions of the present invention are applicable to the lipophilic compounds as defined in this invention.

INFORMATION DISCLOSURE

The International Publication No. WO 95/30670 discloses pyranone compounds useful to treat retroviral infections.

The International Publication No. WO 96/39142 discloses compositions which increase the bioavailability of protease inhibitors.

UK Patent Application, GB 2,222,770A discloses pharmaceutical compositions comprising a cyclosporin in microemulsion pre-concentrate and microemulsion form.

UK Patent Application, GB 2,228,198A discloses pharmaceutical compositions comprising a cyclosporin as active ingredient, a fatty acid triglyceride, a glycerol fatty acid partial ester or propylene glycol or sorbitol complete or partial ester and a tenside having an HLB of at least 10.

UK Patent, GB 2,257,359B discloses pharmaceutical compositions suitable for oral administration comprising a cyclosporin, 1,2-propylene glycol, a mixed mono-, di-, and tri-glyceride and a hydrophilic surfactant.

U.S. Pat. No. 4,230,702 discloses a readily enterally absorbable pharmaceutical composition of pharmacologically active agents, which per se are poorly enterally absorbable.

SUMMARY OF THE INVENTION

One object of the present invention is to provide a pharmaceutical composition comprising a lipophilic, pharmaceutically active agent which possesses high oral bioavailability.

A further object of the present invention is to provide a pharmaceutical composition containing a high drug load of a lipophilic, pharmaceutically active agent for convenient administration.

Another object of the present invention is to provide pharmaceutical compositions which exhibit adequate physical and chemical stability in a self-emulsifying formulation.

Still another object of the present invention is to provide a liquid composition for soft elastic capsules.

The objects of the present invention have been accomplished in that the present invention provides pharmaceutical compositions in a self-emulsifying formulation which allow a high loading of lipophilic compounds (up to about 400 mg/g) while at the same time achieving good oral bioavailability.

The present invention specifically provides a pharmaceutical composition based on the use of a particular oil phase which comprises:

(a) a lipophilic, pharmaceutically active agent,
(b) a mixture of diglyceride and monoglyceride in a ratio of from about 9:1 to about 6:4 by weight (diglyceride:monoglyceride) wherein the diglyceride and monoglyceride are mono- or di- unsaturated fatty acid esters of glycerol having sixteen to twenty-two carbon chain length, (c) one or more pharmaceutically acceptable solvents, and (d) one or more pharmaceutically acceptable surfactants.

DETAILED DESCRIPTION OF THE INVENTION

In accordance with the present invention, there are pharmaceutical compositions comprising a pyranone compound as a pharmaceutically active agent in a self-emulsifying formulation vehicle.

For the purpose of the present invention, the term "pyranone compounds" refers to compounds of formula II

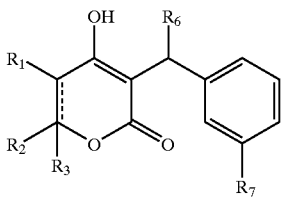

II wherein $R_1$ is —H; $R_2$ is $C_3$–$C_5$ alkyl, phenyl-$(CH_2)_2$—, het-$SO_2NH$—$(CH_2)_2$—, cyclopropyl-$(CH_2)_2$—, F-phenyl-$(CH_2)_2$—, het-$SO_2NH$-phenyl-, or $F_3C$—$(CH_2)_2$—; or $R_1$ and $R_2$ taken together are a double bond; $R_3$ is $R_4$—$(CH_2)_n$—$CH(R_5)$—, $H_3C$—$[O(CH_2)_2]_2$—$CH_2$—, $C_3$–$C_5$ alkyl, phenyl-$(CH_2)_2$—, het-$SO_2NH$—$(CH_2)_2$—, $(HOCH_2)_3C$—$NH$—$C(O)$—$NH$—$(CH_2)_3$—, $(HO_2C)(H_2N)CH$—$(CH_2)_2$—$C(O)$—$NH$—$(CH_2)_3$—, piperazin-1-yl-$C(O)$—$NH$—$(CH_2)_3$, $HO_3S(CH_2)_2$—$N(CH_3)$—$C(O)$—$(CH_2)_6$—$C(O)$—$NH$—$(CH_2)_3$—, cyclopropyl-$(CH_2)_2$—, F-phenyl-$(CH_2)_2$—, het-$SO_2NH$-phenyl, or $F_3C$—$(CH_2)_2$—; n is 0, 1 or 2; $R_4$ is phenyl, het, cyclopropyl, $H_3C$—$[O(CH_2)_2]_2$—, het-$SO_2NH$—, Br—, $N_3$—, or $HO_3S(CH_2)_2$—$N(CH_3)$—$C(O)$—$(CH_2)_6$—$(O)$—$NH$—; $R_5$ is —$CH_2$—$CH_3$, or —$CH_2$-cyclopropyl; $R_6$ is cyclopropyl, $CH_3$—$CH_2$—, or t-butyl; $R_7$ is —$NR_8SO_2$-het, —$NR_8SO_2$-phenyl, optionally substituted with $R_9$, —$CH_2$—$SO_2$-phenyl, optionally substituted with $R_9$, or —$CH_2$—$SO_2$-het; $R_8$ is —H, or —$CH_3$; $R_9$ is —CN, —F, —OH, or —$NO_2$; wherein het is a 5-, 6- or 7-membered saturated or unsaturated ring containing from one to three heteroatoms selected from the group consisting of nitrogen, oxygen and sulfur; and including any bicyclic group in which any of the above heterocyclic rings is fused to a benzene ring or another heterocycle, optionally substituted with —$CH_3$, —CN, —OH, —$C(O)OC_2H_5$, —$CF_3$, —$NH_2$, or —$C(O)$—$NH_2$; or a pharmaceutically acceptable salt thereof. The preferred compound of formula II is a compound of formula I.

The term "pyranone compounds" also refers to compounds of formula III and formula IV

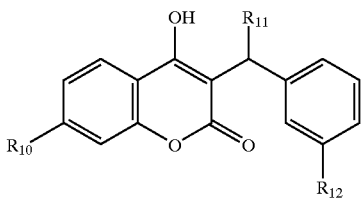

III

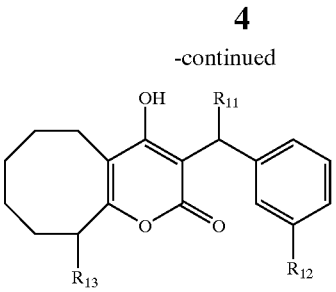

IV wherein $R_{10}$ is —H, $CH_3O$—, or $CH_3O$—$[(CH_2)_2O]_3$—; $R_{11}$ is cyclopropyl, or —$CH_2$—$CH(CH_3)_2$; $R_{12}$ is —$NR_{14}SO_2$-phenyl, optionally substituted with $R_{15}$, —$NR_{14}SO_2$-het, —$CH_2$—$SO_2$-phenyl, optionally substituted with $R_{15}$, or —$CH_2$—$SO_2$-het; $R_{13}$ is —H, —$(CH_2)_2$—$CH_3$, —$CH_2$-cyclopropyl, or —$CH_2$-phenyl; $R_{14}$ is —H, or —$CH_3$; $R_{15}$ is —CN, —F, —$CH_3$, —COOH, or —OH; het is a 5-, 6- or 7-membered saturated or unsaturated ring containing from one to three heteroatoms selected from the group consisting of nitrogen, oxygen and sulfur; and including any bicyclic group in which any of the above heterocyclic rings is fused to a benzene ring or another heterocycle; optionally substituted with one or two —$CH_3$, —CN, —$C(O)OC_2H_5$, or —OH; or a pharmaceutically acceptable salt thereof.

These compounds inhibit retroviral protease and thus inhibit the replication of the virus. They are useful for treating patients infected with human retrovirus such as human immunodeficiency virus (strains of HIV-1 or HIV-2) or human T-cell leukemia viruses (HTLV-I or HTLV-II) which results in acquired immunodeficiency syndrome (AIDS) and/or related diseases. The compounds of formulas I, II, III, and IV are disclosed and claimed in International Application No. PCT/US95/05219, incorporated herein by reference, and may be prepared according to the procedures described in International Publication No. WO 95/30670. In particular, the pyranone compound of formula I has been found to be especially effective as an inhibitor of retroviral protease.

The term "lipophilic compounds" used herein refers to compounds with a LOG P≧2, (LOG P value is measured by its distribution behavior in a biphasic system such as the partition coefficient between the octanol and water phases; it is either determined experimentally or calculated by commercially available software), a low intrinsic aqueous solubility (≦0.1 mg/ml) in the pH range of 1 to 8, and having a solubility in the self-emulsifying formulation vehicle of the present invention greater than 1 mg/ml.

Typical examples of lipophilic compounds which are suitable being used in the present invention include, but not limit to, pyranone compounds of formulas I, II, III, or IV; Cyclosporins such as the naturally occurring cyclosporins A through Z as well as various non-natural cyclosporin derivatives or synthetic cyclosporins; lipophilic steroids such as Medroxyprogesterone Acetate, Progesterone or Testosterone, Thiazolidinediones such as Troglitazone or Pioglitazone; sulfonylureas such as Glyburide; azoles such as Ketoconazole or Itraconazole; camptothecins such as Camptothecin, SN-38 or Irinotecan hydrochloride (also under the name CPT-11); taxanes such as Paclitaxel, Docetaxel or PNU-1; prostaglandins such as $PGE_{2\alpha}$, $PGE_1$ or $PGE_2$; Delavirdine mesylate, Vitamin E (α-tocopherol), Tirilazad Mesylate, Griseofulvin, Phenytoin, Ibuprofen, Flurbiprofen, PNU-2, PNU-3, or PNU-4.

The term "SN-38" refers to a chemical compound under the name (4S)—4,11-diethyl-4,9-dihydroxy-1H-pyrano[3',4':6,7]indolizino[1,2-b]quinoline-3,14(4H,12H)-dione.

The term "PNU-1" refers to a chemical compound under the name [2aR-[2aα,4aβ,6β,7β,9(αR*,βS*), 11α, 12α, 12aα, 12bα]]-6,12b-bis(acetyloxy)-12-(benzoyloxy)-2a,4a, 5,6,7,10,11,12, 12a,12b-decahydro-11-hydroxy-4a, 8,13,13-tetramethyl-5-oxo-7,11-methano-1H-cyclodeca[3,4]benz[1, 2-b]oxet-9-yl β-[[[(1,1-dimethylethyl)amino]carbonyl] amino]-α-hydroxy benzenepropanoate, or (1S,2S,3R,4S,7R, 10R,12R)-4,12-bis(acetyloxy)-15-[((2R,3S)-3-{[(tert-butylamino)carbonyl]amino}-2-hydroxy-3-phenylpropanoyl)oxy]-1-hydroxy-10,14,17,17-tetramethyl-11-oxo-6-oxatetracyclo[11.3.1.0$^{3,10}$.0$^{4,7}$[heptadeca-8,14-dien-2-yl benzoate.

The term "PNU-2" refers to a chemical compound under the name 1-[(2,4-di-1-pyrrolidinyl-9H-pyrimido[4,5-b] indol-9-yl)acetyl]pyrrolidine, or 2-[2,4-di(1-pyrrolidinyl)-9H-pyrimido[4,5-b]indol-9-yl]-1-(1-pyrrolidinyl)-1-ethanone.

The term "PNU-3" refers to a chemical compound under the name (S)-1-[2-[4-[4-(aminocarbonyl)phenyl]-1-piperazinyl]ethyl]-3,4-dihydro-N-methyl-1H-2-benzopyran-6-carboxamide, or 1H-2-Benzopyran-6-carboxamide, 1-[2-[4-[4-(aminocarbonyl)phenyl]-1-piperazinyl]ethyl]-3,4-dihydro-N-methyl-, (S)- or (1S)-1-(2-{4-[4-(aminocarbonyl)phenyl]-1-piperazinyl}ethyl)-N-methyl-3,4-dihydro-1H-isochromene-6-carboxamide.

The term "PNU-4" refers to a chemical compound under the name (−)-6-Chloro-2-[(1-furo [2,3-c]pyridin-5-ylethyl) thio]-4-pyrimidinamine, or 6-chloro-2-{[(1S)-1-furo[2,3-c] pyridin-5-ylethyl]sulfonyl}-4-pyrimidinylamine.

All these pharmaceutically active agents are known in the art and can be readily obtained or be prepared according to known methods.

For example, naturally occurring cyclosporins can be obtained according to the procedure described in Traber et al. 1, Helv. Chim. Acta. 60, 1247–1255 (1977); Traber et al. 2, Helv. Chim. Acta. 65 No. 162, 1655–1667 (1982); Kobel et al., Europ. J. Applied Microbiology and Biotechnology 14, 273–240 (1982); and von Wartburg et al., Progress in Allergy, No. 38, 28–45 (1986)].

Non-natural cyclosporin derivatives or synthetic cyclosporins can be prepared according to the procedure described in U.S. Pat. Nos. 4,108,985, 4,210,581 and 4,220, 641; European Patent Publication Nos. 0 034 567 and 0 056 782; International Patent Publication No. WO 86/02080; Wenger 1, Transp. Proc. 15, Suppl. 1:2230 (1983); Wenger 2, Angew. Chem. Int. Ed., 24, 77 (1985); and Wenger 3, Progress in the Chemistry of Organic Natural Products 50, 123 (1986).

Progesterone and Testosterone are commonly known and have been discussed in numerous publications.

Camptothecin can be obtained from the stem wood of the Chinese tree following the procedure described in M. E. Wall et al., J. Am. Chem. Soc., vol. 88, p. 3888 (1966). Camptothecin may also be prepared according to the procedure described in E. J. Corey, et al., ibid. 40. p. 2140 (1975); Stork, Schultz, J. Am. Chem. Soc., vol. 93, p. 4074 (1971); J. C. Bradley, G. Buchi, J. Org. Chem., vol. 41, p. 699 (1976).; T. Kametani et al., J. Chem. Soc. Perkin Trans. I, p. 1563 (1981).

Troglitazone can be prepared according to the procedure disclosed in U.S. Pat. No. 4,572,912.

Pioglitazone can be prepared according to the procedure disclosed in U.S. Pat. No. 4,687,777.

Ketoconazole can be prepared according to the procedure disclosed in U.S. Pat. Nos. 4,144,346 and 4,223,036.

Glyburide can be prepared according to the procedure disclosed in U.S. Pat. No. 3,454,635.

Griseofulvin can be prepared according to the procedures disclosed in U.S. Pat. No. 3,069,328, U.S. Pat. No. 3,069, 329 and Grove et al., Chem. & Ind. (London), p. 219 (1951); and J. Chem. Soc., p. 3977 (1952).

Itraconazole can be prepared according to the procedure disclosed in U.S. Pat. No. 4,267,179.

Paclitaxel can be prepared according to the procedure disclosed in R. A. Holton et al., J. Am. Chem. Soc., vol. 110, p. 6558 (1988); K. C. Nicolaou et al., Nature, vol. 367, p. 630 (1994); D. G. I. Kingston et al., Studies in Organic Chemistry, vol. 26, entitled "New Trends in Natural Products Chemistry 1986", Attaur-Rahman, P. W. Le Quesne, Eds. (Elsevier, Amsterdam, 1986), pp. 219–235.

Medroxyprogesterone Acetate can be prepared according to the procedure disclosed in U.S. Pat. No. 3,359,287.

Tirilazad Mesylate can be prepared according to the procedure disclosed in U.S. Pat. No. 5,175,281.

Delavirdine can be prepared according to the procedure disclosed in PCT International Patent Application 91/09, 849.

PNU-1 can be prepared according to the procedure disclosed in R. A. Johson et.al., J. Med. Chem. vol. 40, pp 2810–2812 (1997).

PNU-2 can be prepared according to the procedure disclosed in International Publication No. WO 93/20078.

PNU-3 can be prepared according to the procedure disclosed in International Publication No. WO 97/02259.

PNU-4 can be prepared according to the procedure disclosed in International Publication No. WO 96/135678.

Ibuprofen can be prepared according to the procedure disclosed in U.S. Pat. No. 3,228,831 and 3,385,886.

Flurbiprofen can be prepared according to the procedure disclosed in U.S. Pat. No. 3,755,427.

Phenytoin can be prepared according to the procedure disclosed in U.S. Pat. No. 2,409,754.

Irinotecan hydrochloride (CPT-11) can be prepared according to the procedure disclosed in U.S. Pat. No. 4,604,463.

$PGE_1$ can be prepared according to the procedure disclosed in E.J.Corey, et al, J.Am. Chem. Soc., 90, 3245–3247 (1968).

$PGE_2$ can be prepared according to the procedure disclosed in U.S. Pat. No. 3,598,858.

$PGF_2$ can be prepared according to the procedure disclosed in U.S. Pat. No. 3,657,327.

The term "self-emulsifying formulation" used herein refers to a concentrated composition capable of generating emulsions or microemulsions upon mixing with sufficient aqueous media.

The emulsions or microemulsions generated from the present invention are conventional solutions comprising a hydrophilic phase and a lipophilic phase. Microemulsions are also characterized by their thermodynamic stability, optical transparency and small average droplet size, generally less than about 0.15 micron.

The term "self-emulsifying formulation vehicle" refers to a composition comprising a mixture of diglyceride and monoglyceride in a ratio of from about 9:1 to about 6:4 by wight (diglyceride:monoglyceride) wherein the diglyceride and monoglyceride are mono- or di- unsaturated fatty acid esters of glycerol having sixteen to twenty-two carbon chain length, one or more pharmaceutically acceptable solvents, and one or more pharmaceutically acceptable surfactants. Optionally, the self-emulsifying formulation vehicle may further comprise a basic amine.

Diglyceride of the present invention refers to a fatty acid ester of glycerol having structure formula $HOCH_2$—CH ($O_2CR$)—$CH_2$($O_2CR$) or ($RCO_2$)$CH_2$—H(OH)—$CH_2$ ($O_2CR$), wherein R is mono-unsaturated or di-unsaturated alkyl group having fifteen to twenty-one carbon atoms. The preferred diglyceride is diolein (R is mono-unsaturated alkyl group with seventeen carbon atoms), dilinoleate (R is di-unsaturated alkyl group with seventeen carbon atoms), or a mixture of diolein and dilinoleate. The most preferred diglyceride is diolein.

Monoglyceride of the present invention refers to a fatty acid ester of glycerol having structure formula $HOCH_2$—H(OH)—$CH_2$($O_2CR$) or $HOCH_2$-H($O_2CR$)—$CH_2OH$, wherein R is a mono-unsaturated or di-unsaturated alkyl group having fifteen to twenty-one carbon atoms. The preferred monoglyceride is monoolein (R is mono-unsaturated alkyl group with seventeen carbon atoms), monolinoleate (R is di-unsaturated alkyl group with seventeen carbon atoms), or a mixture of monoolein and monolinoleate. The most preferred monoglyceride is monoolein.

The mixture of diglyceride and monoglyceride may be prepared by mixing individual diglyceride and monoglyceride in appropriate relative proportion, by partial hydrolysis of triglyceride, or transesterification reaction of triglycerides, diglycerides with glycerol.

All of the glycerides of the present invention are known and can be prepared by conventional methods.

The amount of active ingredient in the composition may vary or be adjusted widely depending on the intended route of administration, the potency of the particular active ingredient being used, the severity of the illness and the required concentration. If desired, however, a lipophilic pharmaceutically active agent can be present in the self-emulsifying formulation vehicle of the present invention in an amount up to about 400 mg/g with excellent dispersability and high oral bioavailability in vivo typically reaching 70–84% in rats.

The compositions of the present invention with high oral bioavailability (84% in rats) demonstrate an almost transparent or translucent solution upon dilution with water, which indicates that a microemulsion is formed.

The compositions of the present invention with moderately high bioavailability (60–70% in rats) usually show a visible fine white emulsion without precipitation of the drug upon dilution with water, which indicates that an emulsion is formed.

In one aspect, the present invention specifically provides a pharmaceutical composition based on the use of particular oil phase which comprises:

(a) a pyranone compound of formulas I, II, III or IV as a pharmaceutically active agent, (b) a mixture of diglyceride and monoglyceride in a ratio of from about 9:1 to about 6:4 by weight (diglyceride:monoglyceride) wherein the diglyceride and monoglyceride are mono- or di- unsaturated fatty acid esters of glycerol having sixteen to twenty-two carbon chain length, (c) one or more pharmaceutically acceptable solvents, and (d) one or more pharmaceutically acceptable surfactants.

In another aspect, the present invention provides a pharmaceutical composition based on the use of particular oil phase which comprises:

(a) a lipophilic, pharmaceutically active agent selected from the group consisting of Cyclosporins, Medroxyprogesterone Acetate, Progesterone, Testosterone, Troglitazone, Pioglitazone, Glyburide, Ketoconazole, Itraconazole, camptothecin, SN-38, Irinotecan hydrochloride, Paclitaxel, Docetaxel, PNU-1, $PGE_{2\alpha}$, $PGE_1$, $PGE_2$, Delavirdine mesylate, Vitamin E, Tirilazad Mesylate, Griseofulvin, Phenytoin, Ibuprofen, Flurbiprofen, PNU-2, PNU-3 and PNU-4, (b) a mixture of diglyceride and monoglyceride in a ratio of from about 9:1 to about 6:4 by weight (diglyceride:monoglyceride) wherein the diglyceride and monoglyceride are mono- or di- unsaturated fatty acid esters of glycerol having sixteen to twenty-two carbon atom chain length, (c) one or more pharmaceutically acceptable solvents, and (d) one or more pharmaceutically acceptable surfactants.

In addition, the compositions may further comprise a pharmaceutically acceptable amine.

The term "pharmaceutically acceptable" used herein refers to those properties which are biologically compatible with the treated subjects from a pharmacological and toxicological point of view.

Solvents of the present invention refer to propylene glycol, polypropylene glycol, polyethylene glycol (such as PEG300, 400, 600, etc.), glycerol, ethanol, triacetin, dimethyl isosorbide, glycofurol, propylene carbonate, water, dimethyl acetamide or a mixture thereof.

The preferred solvent is propylene glycol or a mixture comprising propylene glycol and 95% (v/v) ethanol (hereinafter ethanol). In the mixture of propylene glycol and ethanol, propylene glycol is in an amount of from about 50% to about 95%.

Surfactants of the present invention refer to non-ionic surfactants including Polyoxyl 40 hydrogenated castor oil sold under the trade name, among the others, Cremophor RH40; Polyoxyl 35 castor oil sold under the trade name, among the others, Cremophor EL or Cremophor EL-P; Polysorbates; Solutol HS-15; Tagat TO; Peglicol 6-oleate; Polyoxyethylene stearates; Saturated Polyglycolyzed Glycerides; or Poloxamers; all of which are commercially available. The preferred surfactant is Cremophor RH40 or Cremophor EL.

Saturated Polyglycolyzed Glycerides used herein include Gelucire 44/14 or Gelucire 50/13.

Polyoxyethylene stearates used herein include Poloxyl 6 stearate, Poloxyl 8 stearate, Poloxyl 12 stearate and Poloxyl 20 stearate.

Poloxamers used herein include Poloxamer 124 and Poloxamer 188.

Polysorbates used herein include Polysorbate 20, Polysorbate 40, Polysorbate 60 and Polysorbate 80.

The term "amine" used herein refers to lower alkylamines such as, for example, ethanolamine, diethanolamine, triethanolamine, dimethylaminoethanol, tris (hydroxymethyl)aminomethane or ethylenediamine; quaternary ammoniums such as, for example, choline hydroxide; basic amino acids such as, for example, arginine lysine or guanidine. The preferred lower alkylamine is dimethylaminoethanol or tris(hydroxymethyl)aminomethane.

A typical composition of the invention comprises:

(a) a lipophilic, pharmaceutically active agent, in an amount of from about 1% to about 40% by weight of the total composition, (b) a mixture of diglyceride and monoglyceride in a ratio of from about 9:1 to about 6:4 by weight (diglyceride:monoglyceride) wherein the diglyceride and monoglyceride are mono- or di- unsaturated fatty acid esters of glycerol having sixteen to twenty-two carbon chain length in an amount of from about 5% to about 40% by weight of the total composition, (c) one or more pharmaceutically acceptable solvents in an amount of from about 10% to about 30% by weight of the total composition, and (d) a pharmaceutically acceptable surfactant in an amount of from about 10% to about 50% by weight of the total composition.

Optionally, the above composition may further comprise a amine in an amount of from about 0.1% to 10% by weight of the total composition.

The preferred lipophilic compounds are pyranone compounds of formulas I, II, III, IV or cyclosporin A.

A preferred composition of the invention comprises:

(a) a lipophilic, pharmaceutically active agent, in an amount of from about 5% to about 30% by weight of the total composition, (b) a mixture of diolein and monoolein in a ratio of about 9:1 by weight (diolein:monoolein) in an amount of from about 5% to about 35% by weight of the total composition, (c) a solvent comprising propylene glycol or a mixture of propylene glycol and ethanol in an amount of from about 15% to about 25% by weight of the total composition, and (d) a surfactant comprising Cremophor RH40 or Cremophor EL in an amount of from about 30% to about 45% by weight of the total composition.

Another preferred composition of the invention comprises:

(a) a lipophilic, pharmaceutically active agent, in an amount of from about 5% to about 30% by weight of the total composition, (b) a mixture of diolein and monoolein in a ratio of about 8:2 by weight (diolein:monoolein) in an amount of from about 5% to about 35% by weight of the total composition, (c) a solvent comprising propylene glycol or a mixture of propylene glycol and ethanol in an amount of from about 15% to about 25% by weight of the total composition, and (d) a surfactant comprising Cremophor RH40 or Cremophor EL in an amount of from about 30% to about 45% by weight of the total composition.

Optionally, the preferred compositions further comprise a amine in an amount of about 0.1% to about 7% by weight of the total composition.

In the preferred compositions of the present invention, an even more preferred composition comprises a pyranone compound of formula I in an amount of from about 20% to about 30% by weight to the total composition.

In the preferred compositions of the present invention, an even more preferred composition comprises cyclosporin A in an amount of from about 5% to about 15% by weight to the total composition.

In the preferred compositions of the present invention, the mixture of propylene glycol and ethanol is in a ratio of about 1:1.

In the preferred compositions of the present invention, an even more preferred composition comprises a dimethylaminoethanol, tris(hydroxymethyl)aminomethane in an amount of from about 0.1% to 7% by weight of the total composition.

In the preferred compositions of the present invention, an even more preferred composition comprises a mixture of diolein and monoolein in a ratio of about 8:2.

In particular, the most preferred composition of the present invention comprises the pyranone compound of formula I.

The composition of the present invention may take the form of liquid for soft elastic capsules or hard gelatin capsules by oral application. The composition may also be in the form of a liquid solution for oral, parenteral, rectal or topical application. The preferred dosage form is in the form of liquid for soft elastic capsules.

If desired, the compositions of the present invention may further comprise conventional pharmaceutical additives such as co-surfactants(for example sodium lauryl sulfate), coloring agents, flavoring agents, fragrances, preserving agents, stabilizers, anti-oxidant and/or thickening agents.

The compositions of the present invention may be prepared in a conventional manner, for example, by dissolving an active agent in the solvent, then adding the oil phase, the surfactant, and optionally the basic amine. The resulting solution is then formulated into the desired dosage form such as, for example, soft elastic capsules or hard gelatin capsules by known manufacturing technology.

The pharmaceutical compositions of the present invention will be better understood in connection with the following examples, which are intended as an illustration of and not a limitation upon the scope of the invention. Without further elaboration, it is believed that one skilled in the art can, using the preceding description and the information provided in the examples below, practice the present invention to its fullest extent.

A. General Procedure for Preparing the Compositions of the Present Invention.

Drug is placed in a container. A solvent comprising propylene glycol or a mixture of solvents selected from ethanol (95%) and propylene glycol (1:1 by weight) is added and the cap is tightened. The container is put in a water bath at about 60° C. and shaken gently until all of the drug material is dissolved. After the container is cooled to room temperature, appropriate amounts of a mixture of diglyceride (such as diolein) and monoglyceride (such as monoolein), a surfactant (such as Cremophor RH40 or Cremophor EL) and optionally a basic amine (such as ethanolamine or diethanolamine) are added into the container. The container is sealed and put in a water bath at about 60° C. and shaken gently until a clear solution is formed. The container is usually left at ambient conditions for future use.

EXAMPLE 1

| Component | Weight (mg) | % w/w |
| --- | --- | --- |
| The compound of formula I | 302 | 26.4 |
| EtOH/Propylene Glycol (1:1) | 197 | 17.3 |
| Diolein/monoolein (8:2) | 259 | 22.7 |
| Cremophor RH40 | 307 | 26.9 |
| Ethanolamine | 61 | 5.3 |
| Sodium lauryl sulfate | 16 | 1.4 |

EXAMPLE 2

| Component | Weight (mg) | % w/w |
| --- | --- | --- |
| The compound of formula I | 302 | 27.9 |
| EtOH/Propylene Glycol (1:1) | 280 | 19.2 |
| Diolein/monoolein (8:2) | 250 | 23.1 |
| Cremophor RH40 | 304 | 28.0 |
| Sodium lauryl sulfate | 18 | 1.6 |

EXAMPLE 3

| Component | Weight (mg) | % w/w |
|---|---|---|
| The compound of formula I | 202 | 20.4 |
| EtOH/Propylene Glycol (1:1) | 198 | 20.0 |
| Diolein/monoolein (9:1) | 90 | 9.0 |
| Cremophor EL | 502 | 50.6 |

EXAMPLE 4

| Component | Weight (mg) | % w/w |
|---|---|---|
| The compound of formula I | 302 | 29.0 |
| EtOH/Propylene Glycol (1:1) | 210 | 20.2 |
| Diolein/monoolein (9:1) | 60 | 5.8 |
| Cremophor EL | 450 | 43.4 |
| Diethanolamine | 16 | 1.5 |

EXAMPLE 5

| Component | Weight (mg) | % w/w |
|---|---|---|
| The compound of formula I | 200 | 16.6 |
| EtOH/Propylene Glycol (1:1) | 212 | 17.6 |
| Diolein/monoolein (8:2) | 380 | 31.5 |
| Cremophor RH40 | 365 | 30.2 |
| α-tocopherol | 48 | 4.0 |

EXAMPLE 6

| Component | Weight (mg) | % w/w |
|---|---|---|
| The compound of formula I | 298 | 25.8 |
| EtOH/Propylene Glycol (1:1) | 198 | 17.2 |
| Diolein/monoolein (8:2) | 287 | 24.8 |
| Cremophor RH40 | 325 | 28.2 |
| dimethylaminoethanol | 45 | 3.9 |

EXAMPLE 7

| Component | Weight (mg) | % w/w |
|---|---|---|
| The compound of formula I | 299 | 27.9 |
| EtOH/Propylene Glycol (1:1) | 152 | 14.2 |
| Diolein/monoolein (8:2) | 249 | 23.2 |
| Cremophor RH40 | 304 | 28.4 |
| Choline hydroxide | 66 | 6.2 |

EXAMPLE 8

| Component | Weight (mg) | % w/w |
|---|---|---|
| The compound of formula I | 298 | 27.6 |
| EtOH/Propylene Glycol (1:1) | 150 | 13.9 |
| Diolein/monoolein (8:2) | 257 | 23.8 |
| Cremophor EL | 309 | 28.7 |
| Ethanolamine | 62 | 5.8 |

EXAMPLE 9

| Component | Weight (mg) | % w/w |
|---|---|---|
| The compound of formula I | 197 | 19.7 |
| EtOH/Propylene Glycol (1:1) | 208 | 20.8 |
| Diolein/monoolein (8:2) | 271 | 27.1 |
| Cremophor EL | 329 | 32.9 |

EXAMPLE 10

| Component | Weight (mg) | % w/w |
|---|---|---|
| The compound of formula I | 202 | 20.0 |
| EtOH/Propylene Glycol (1:1) | 208 | 20.6 |
| Diolein/monoolein (9:1) | 279 | 27.6 |
| Cremophor EL | 321 | 31.8 |

EXAMPLE 11

| Component | Weight (mg) | % w/w |
|---|---|---|
| The compound of formula I | 202 | 19.8 |
| EtOH/Propylene Glycol (1:1) | 201 | 19.7 |
| Diolein/monoolein (9:1) | 96 | 9.4 |
| Polysorbate 80 | 522 | 51.1 |

EXAMPLE 12

| Component | Weight (mg) | % w/w |
|---|---|---|
| The compound of formula I | 213 | 21.0 |
| EtOH/Propylene Glycol (1:1) | 200 | 19.8 |
| Diolein/monoolein (9:1) | 86 | 8.5 |
| Cremophor EL | 514 | 50.7 |

EXAMPLE 13

| Component | Weight (mg) | % w/w |
|---|---|---|
| The compound of formula I | 301 | 29.3 |
| EtOH/Propylene Glycol (1:1) | 200 | 19.5 |
| Diolein/monoolein (8:2) | 204 | 19.9 |
| Cremophor EL | 261 | 25.4 |
| Diethanolamine | 61 | 5.9 |

EXAMPLE 14

| Component | Weight (mg) | % w/w |
|---|---|---|
| The compound of formula I | 400 | 40 |
| EtOH | 100 | 10 |
| Diolein/monoolein (8:2) | 70 | 7 |
| Cremophor EL | 330 | 33 |
| Diethanolamine | 80 | 8 |
| $H_2O$ | 20 | 2 |

EXAMPLE 15

| Component | Weight (mg) | % w/w |
|---|---|---|
| The compound of formula I | 300 | 30 |
| EtOH/Propylene Glycol (1:1) | 190 | 19 |
| Diolein/monoolein (8:2) | 180 | 18 |
| Cremophor EL | 250 | 25 |
| Water | 28 | 2.86 |
| Propyl Gallate | 2 | 0.2 |
| Diethanolamine | 50 | 5 |

EXAMPLE 16

| Component | Weight (mg) | % w/w |
|---|---|---|
| The compound of formula I | 200 | 20 |
| EtOH/Propylene Glycol (1:1) | 200 | 20 |
| Diolein/monoolein (8:2) | 120 | 12 |
| Gelucire 44/14 | 480 | 48 |

EXAMPLE 17

| Component | Weight (mg) | % w/w |
|---|---|---|
| The compound of formula I | 200 | 20 |
| EtOH/Propylene Glycol (1:1) | 200 | 20 |
| Diolein/monoolein (8:2) | 120 | 12 |
| Polysorbate 80 | 480 | 48 |

EXAMPLE 18

| Component | Weight (mg) | % w/w |
|---|---|---|
| The compound of formula I | 200 | 20 |
| EtOH/Propylene Glycol (1:1) | 200 | 20 |
| Diolein/monoolein (7:3) | 120 | 12 |
| Cremophor EL | 480 | 48 |

EXAMPLE 19

| Component | Weight (mg) | % w/w |
|---|---|---|
| The compound of formula I | 200 | 20 |
| EtOH/Propylene Glycol (1:1) | 200 | 20 |
| Diolein/monoolein (6:4) | 120 | 12 |
| Cremophor EL | 480 | 48 |

EXAMPLE 20

| Component | Weight (mg) | % w/w |
|---|---|---|
| The compound of formula I | 300 | 30 |
| 95% EtOH | 95 | 9.5 |
| Propylene glycol | 80 | 8 |
| Diolein/monoolein (8:2) | 70 | 7 |
| Cremophor EL | 455 | 45.5 |

EXAMPLE 21

| Component | Weight (mg/g) | % w/w |
|---|---|---|
| Cyclosporin A | 100 | 10 |
| EtOH/Propylene glycol (1:1) | 200 | 20 |
| Cremophor EL | 400 | 40 |
| Diolein/monoolein (8:2) | 300 | 30 |

EXAMPLE 22

| Component | Weight (mg/g) | % w/w |
|---|---|---|
| Cyclosporin A | 100 | 10 |
| EtOH/Propylene glycol (1:1) | 200 | 20 |
| Cremophor EL | 400 | 40 |
| Diolein/monoolein (9:1) | 300 | 30 |

EXAMPLE 23

| Component | Weight (mg/g) | % w/w |
|---|---|---|
| Cyclosporin A | 100 | 10 |
| EtOH/Propylene glycol (1:1) | 200 | 20 |
| Cremophor EL | 400 | 40 |
| Diolein/monoolein (7:3) | 300 | 30 |

EXAMPLE 24

| Component | Weight (mg/g) | % w/w |
|---|---|---|
| Cyclosporin A | 100 | 10 |
| EtOH/Propylene glycol(1:1) | 200 | 20 |
| Cremophor EL | 400 | 40 |
| Diolein/monoolein (6:4) | 300 | 30 |

EXAMPLE 25

| Component | Weight (mg/g) | % w/w |
|---|---|---|
| Cyclosporin A | 100 | 10 |
| EtOH/Propylene glycol(1:1) | 200 | 20 |
| Cremophor EL-P | 400 | 40 |
| Diolein/monoolein (8:2) | 300 | 30 |

EXAMPLE 26

| Component | Weight (mg/g) | % w/w |
|---|---|---|
| Cyclosporin A | 100 | 10 |
| EtOH/Propylene glycol(1:1) | 200 | 20 |
| Cremophor RH40 | 400 | 40 |
| Diolein/monoolein (8:2) | 300 | 30 |

EXAMPLE 27

| Component | Weight (mg/g) | % w/w |
|---|---|---|
| Cyclosporin A | 100 | 10 |
| EtOH/Propylene glycol(1:1) | 200 | 20 |
| Solutol HS-15 | 400 | 40 |
| Diolein/monoolein (8:2) | 300 | 30 |

EXAMPLE 28

| Component | Weight (mg/g) | % w/w |
|---|---|---|
| Cyclosporin A | 100 | 10 |
| EtOH/Propylene glycol(1:1) | 200 | 20 |
| Polysorbate 80 | 400 | 40 |
| Diolein/monoolein (8:2) | 300 | 30 |

EXAMPLE 29

| Component | Weight (mg/g) | % w/w |
|---|---|---|
| Cyclosporin A | 100 | 10 |
| EtOH/Propylene glycol(1:1) | 200 | 20 |
| Cremophor EL | 400 | 40 |
| Diolein/monolinoleate (8:2) | 300 | 30 |

EXAMPLE 30

| Component | Weight (mg/g) | % w/w |
|---|---|---|
| Cyclosporin A | 100 | 10 |
| EtOH/Propylene glycol(1:1) | 200 | 20 |
| Cremophor EL | 400 | 40 |
| Diolein/monolinoleate (9:1) | 300 | 30 |

EXAMPLE 31

| Component | Weight (mg/g) | % w/w |
|---|---|---|
| Cyclosporin A | 100 | 10 |
| EtOH/Propylene glycol(1:1) | 200 | 20 |
| Cremophor EL | 400 | 40 |
| Diolein/monolinoleate (7:3) | 300 | 30 |

EXAMPLE 32

| Component | Weight (mg/g) | % w/w |
|---|---|---|
| Cyclosporin A | 100 | 10 |
| EtOH/Propylene glycol(1:1) | 200 | 20 |
| Cremophor EL | 400 | 40 |
| Diolein/monolinoleate (6:4) | 300 | 30 |

EXAMPLE 33

| Component | Weight (mg/g) | % w/w |
|---|---|---|
| α-tocopherol | 100 | 10 |
| EtOH/Propylene glycol(1:1) | 200 | 20 |
| Cremophor EL | 400 | 40 |
| Diolein/monoolein (8:2) | 300 | 30 |

EXAMPLE 34

| Component | Weight (mg/g) | % w/w |
|---|---|---|
| α-tocopherol | 200 | 20 |
| EtOH/Propylene glycol(1:1) | 100 | 10 |
| Cremophor EL | 400 | 40 |
| Diolein/monoolein (8:2) | 300 | 30 |

EXAMPLE 35

| Component | Weight (mg/g) | % w/w |
|---|---|---|
| α-tocopherol | 300 | 30 |
| EtOH/Propylene glycol(1:1) | 100 | 10 |
| Cremophor EL | 340 | 34 |
| Diolein/monoolein (8:2) | 260 | 26 |

EXAMPLE 36

| Component | Weight (mg/g) | % w/w |
|---|---|---|
| α-tocopherol | 400 | 40 |
| EtOH/Propylene glycol (1:1) | 100 | 10 |
| Cremophor EL | 400 | 40 |
| Diolein/monoolein (8:2) | 100 | 10 |

EXAMPLE 37

| Component | Weight (mg/g) | % w/w |
|---|---|---|
| α-tocopherol | 500 | 50 |
| EtOH/Propylene glycol (1:1) | 100 | 10 |
| Cremophor EL | 300 | 30 |
| Diolein/monoolein (8:2) | 100 | 10 |

EXAMPLE 38

| Component | Weight (mg/g) | % w/w |
|---|---|---|
| Tirilazad mesylate | 100 | 10 |
| EtOH/Propylene glycol (1:1) | 200 | 20 |
| Cremophor EL | 400 | 40 |
| Diolein/monoolein (8:2) | 300 | 30 |

EXAMPLE 39

| Component | Weight (mg/g) | % w/w |
|---|---|---|
| Testosterone | 60 | 6 |
| EtOH/Propylene glycol (1:1) | 240 | 24 |
| Cremophor EL | 400 | 40 |
| Diolein/monoolein (8:2) | 300 | 30 |

EXAMPLE 40

| Component | Weight (mg/g) | % w/w |
|---|---|---|
| Pioglitazone hydrochloride | 50 | 5 |
| Dimethyl acetamide | 125 | 12.5 |
| Glycerine | 125 | 12.5 |
| Cremophor EL | 500 | 50 |
| Diolein/monoolein (8:2) | 200 | 20 |

EXAMPLE 41

| Component | Weight (mg/g) | % w/w |
|---|---|---|
| CPT-11 | 50 | 5 |
| Dimethyl isosorbide | 250 | 25 |
| Diethanolamine | 100 | 10 |
| Cremophor EL | 450 | 45 |
| Diolein/monoolein (8:2) | 150 | 15 |

EXAMPLE 42

| Component | Weight (mg/g) | % w/w |
|---|---|---|
| CPT-11 | 60 | 6 |
| Dimethyl acetamide | 250 | 25 |
| Diethanolamine | 50 | 5 |
| Cremophor EL | 450 | 45 |
| Diolein/monoolein (8:2) | 190 | 19 |

EXAMPLE 43

| Component | Weight (mg/g) | % w/w |
|---|---|---|
| CPT-11 | 50 | 5 |
| Propylene glycol | 250 | 25 |
| Dimethylaminoethanol | 50 | 5 |
| Cremophor EL | 370 | 37 |
| Diolein/monoolein (8:2) | 280 | 28 |

EXAMPLE 44

| Component | Weight (mg/g) | % w/w |
|---|---|---|
| Paclitaxel | 60 | 6 |
| EtOH/PEG400 (1:1) | 300 | 30 |
| Cremophor EL | 440 | 44 |
| Diolein/monoolein (8:2) | 200 | 20 |

EXAMPLE 45

| Component | weight (mg) | % w/w |
|---|---|---|
| Ketoconazole | 100 | 8.7 |
| Diolein/Monoolein (8:2) | 343 | 29.8 |
| Cremophor EL | 457 | 39.7 |
| Nicotinamide | 50 | 4.3 |
| Water | 20 | 1.7 |
| EtOH/Propylene Glycol (1:1) | 182 | 15.8 |

EXAMPLE 46

| Component | weight (mg) | % w/w |
|---|---|---|
| Flurbiprofen | 100 | 9.2 |
| Diolein/Monoolein (8:2) | 343 | 31.7 |
| Cremophor EL | 457 | 42.2 |
| EtOH/Propylene Glycol (1:1) | 182 | 16.8 |

EXAMPLE 47

| Component | Weight (mg) | % w/w |
|---|---|---|
| Phenytoin | 25 | 2.3 |
| Diolein/Monoolein (8:2) | 343 | 31.8 |
| Cremophor EL | 457 | 42.4 |
| Nicotinamide | 50 | 4.6 |
| Water | 20 | 1.9 |
| EtOH/Propylene Glycol (1:1) | 182 | 16.9 |

EXAMPLE 48

| Component | Weight (mg) | % w/w |
|---|---|---|
| Progesterone | 20 | 2.0 |
| Capmul MCM | 343 | 34.2 |
| Cremophor EL | 457 | 45.6 |
| EtOH/Propylene Glycol (1:1) | 182 | 18.2 |

EXAMPLE 49

| Component | Weight (mg) | % w/w |
|---|---|---|
| Progesterone | 20 | 2.0 |
| Diolein/Monoolein (8:2) | 343 | 34.2 |
| Cremophor EL | 457 | 45.6 |
| EtOH/Propylene Glycol (1:1) | 182 | 18.2 |

EXAMPLE 50

| Component | Wt (mg) | % w/w |
|---|---|---|
| Ibuprofen | 400 | 28.9 |
| Diolein/Monoolein (8:2) | 343 | 24.8 |
| Cremophor EL | 457 | 33.1 |
| EtOH/Propylene Glycol | 182 | 13.2 |

EXAMPLE 51

| Component | Weight (mg) | % w/w |
|---|---|---|
| $PGF_{2a}$ | 50 | 4.8 |
| Diolein/Monoolein (8:2) | 343 | 33.2 |
| Cremophor EL | 457 | 44.3 |
| EtOH/Propylene Glycol | 182 | 17.6 |

EXAMPLE 52

| Component | Weight (mg) | % w/w |
|---|---|---|
| $PGE_1$ | 10 | 1.0 |
| Diolein/Monoolein (8:2) | 343 | 34.6 |
| Cremophor EL | 457 | 46.1 |
| EtOH/Propylene Glycol | 182 | 18.3 |

EXAMPLE 53

| Component | Weight (mg) | % w/w |
|---|---|---|
| $PGE_2$ | 10 | 1.0 |
| Diolein/Monoolein (8:2) | 343 | 34.6 |
| Cremophor EL | 457 | 46.1 |
| EtOH/Propylene Glycol | 182 | 18.3 |

B. Oral Bioavailability Test.

(i) Sprague-Dawley male rats were selected for the in vivo oral bioavailability study. Each rat was prepared by the surgical implantation of an indwelling cannula in the superior vena cava. Each rat, in the weight range of 300–400 g, was fasted overnight prior to dosing. Each formulation was orally administered to a group of rats (n=3) at a 20 mg/kg dose. The formulations with high concentration of the compound of formula I (typically 200–300 mg/g) was diluted by 100-fold with water and injected directly into the rat's stomach using oral gavage. Serial blood samples of 0.25 ml were obtained from the indwelling cannula at 0.25, 0.5, 1, 2, 4, 6, 8, 12, and 24 hours after dosing. These blood samples were analyzed using a HPLC assay specific for the testing compounds. Drug concentrations in the blood of the test rats are plotted against the time after the drug is administered through an intravenous (i.v.) or oral route and the AUCs (the Area Under the Plasma Concentration-Time Curve) are integrated using the trapezoidal rule to calculate the absolute bioavailability as shown in Table 1.

$$\text{Absolute bioavailability}(F) = \frac{(AUC)_{oral}/Dose_{oral}}{(AUC)_{iv}/Dose_{iv}}$$

(ii) Male Beagle dogs were also selected for the in vivo oral bioavailability study. Each dog, in the weight range of 13.5–17.5 kg, was fasted overnight prior to dosing. Each formulation was orally administered to a group of dogs (n=4) at a 20 mg/kg dose. The formulation of high concentration of the compound of formula I (300 mg/g) was encapsulated in gelatin capsules and administered. Serial blood samples of 2 ml were obtained from the jugular vein at 20, 40 minutes and 1, 2, 4, 6, 8, 12, and 24 hours after dosing. These blood samples were analyzed using a HPLC assay specific for the compound of formula I. The blood concentrations of the compound of formula I are plotted against the time and the AUCs are obtained to calculate the absolute bioavailability. The results are shown in Table 2.

(iii) Ten healthy volunteers were orally administered with eight 150 mg (1200 mg single dose) disodium salt of compound of the formula I encapsulated in hard gelatin capsules as reference. Weeks later, the same group were orally administered with four 300 mg (1200 mg single dose) compound of the formula I in a formulation as exhibited in Example 15. Serial blood samples of two group volunteers were obtained at 30 minutes and 1, 2, 4, 6, 8, 12, and 24 hours after dosing. These blood samples were analyzed using a HPLC assay specific for the compound of formula I. The blood concentrations of the compound of formula I are plotted against the time and the AUCs are obtained to calculate the absolute bioavailability. The results are shown in Table 3.

$$\text{Relative bioavailabity} = AUC_{test}/AUC_{ref} \times 100\%$$

The present invention achieves the desired results as demonstrated by the increased absolute oral bioavailabilities in Tables 1, 2 and 3. In addition, the absolute oral bioavailability of cyclosporin A in the formulation of the Example 21 is 23% determined in rats (N=8).

TABLE 1

Absolute Mean Oral Bioavailability in Rats

| Example No. | Absolute Mean Oral Bioavailability (%) |
|---|---|
| 1 | 84 |
| 2 | 37 |

TABLE 1-continued

Absolute Mean Oral Bioavailability in Rats

| Example No. | Absolute Mean Oral Bioavailability (%) |
|---|---|
| 3 | 71 |
| 4 | 71 |
| Aqueous suspension of free acid of the compound of formula I | <20 |

TABLE 2

Absolute Mean Oral Bioavailability in Dogs

| Example No. | Absolute Mean Oral Bioavailability (%) |
|---|---|
| 12 | 42.7 |
| 13 | 38.6 |
| Free Acid of the compound formula I in Hard Gelatin Capsules | 1.5 |

TABLE 3

Relative Bioavailability in Human (1200 mg Single Dose)

| Formulation | Relative Bioavailability (%) |
|---|---|
| Example 15 | 230 |
| Disodium salt of the compound of formula I in Hard Gelatin Capsules | 100 |

We claim:
1. A pharmaceutical composition comprising;
   (a) a lipophilic, pharmaceutically active agent,
   (b) a mixture consisting essentially of diglyceride and monoglyceride in a ratio of from about 9:1 to about 6:4 by weight (diglyceride:monoglyceride) wherein the diglyceride and monoglyceride are mono- or di-unsaturated fatty acid esters of glycerol having sixteen to twenty-two carbon chain length,
   (c) one or more pharmaceutically acceptable solvents, and
   (d) one or more pharmaceutically acceptable surfactants; wherein the solvent is propylene glycol, polypropylene glycol, polyethylene glycol, glycerol, ethanol, dimethyl isosorbide, glycofurol, propylene carbonate, dimethyl acetamide, or a mixture thereof; wherein said surfactant is Polyoxyl 40 hydrogenated castor oil, Polyoxyl 35 castor oil, polyethylene glycol 12-hydroxy stearate, polyoxyethylene glyceryl trioleate, Peglicol 6-oleate, Polyoxyethylene stearates, Poloxamers, Polysorbates, or Saturated Polyglycolyzed Glycerides; with the proviso that said lipophilic, pharmaceutically active agent has a LOG P value $\geq 2$, an intrinsic aqueous solubility $\leq 0.1$ in the pH range of 1 to 8 and a solubility greater than 1 mg/ml in the mixture of b, c and d as defined herein.

2. The pharmaceutical composition of claim 1 wherein the lipophilic, pharmaceutically active agent is selected from the group consisting of Medroxyprogesterone Acetate, Progesterone, Testosterone, Troglitazone, Pioglitazone, Glyburide, Ketoconazole, Itraconazole, Camptothecin, (4S) 4,11-diethyl-4,9-dihydroxy-1H-pyrano[3',4':6,7]indolizino[1,2-b]quinoline-3,14(4H,12H)-dione, Irinotecan hydrochloride, Paclitaxel, Docetaxel, 2aR-[2aα,4aβ,6β,7β,9(αR*,βS*),11α,12α,12aα,12bα]]-6,12b-bis(acetyloxy)-12-(benzoyloxy)-2a,4a,5,6,7,10,11,12, 12a, 12b-decahydro-11-hydroxy-4a,8,13,13-tetramethyl-5-oxo-7,11-methano-1H-cyclodeca[3,4]benz[1,2-b]oxet-9-yl β-[[[(1,1-dimethylethyl)amino]carbonyl] amino]-α-hydroxy benzenepropanoate, (1S,2S,3R,4S,7R,10R,12R)-4,12-bis(acetyloxy)-15-[((2R,3S)-3-{[(tert-butylamino)carbonyl]amino}-2-hydroxy-3-phenylpropanoyl)oxy]-1-hydroxy-10,14,17,17-tetramethyl-11-oxo-6-oxatetracyclo[11.3.1.0$^{3,10}$.0$^{4,7}$]heptadeca-8,14-dien-2-yl benzoate, $PGE_{2\alpha}$, $PGE_1$, $PGE_2$, Delavirdine mesylate, Vitamin E, Tirilazad Mesylate, Griseofulvin, Phenytoin, Ibuprofen, Flurbiprofen, 1-[(2,4-di(1-pyrrolidinyl)-9H-pyrimido[4,5-b]-yl]indol-9-ylacetyl]-1-(1-pyrrolidine, 2-[2,4-di(1-pyrrolidinyl)-9H-pyrimido[4,5-b]indol-9-yl]-1-(1-pyrrolidinyl)-1-ethanone, (S)-1-[2-[4-[4-(aminocarbonyl)phenyl]-1-piperazinyl]ethyl]-3,4-dihydro-N-methyl-1H-2-benzopyran-6-carboxamide, 1H-2-benzopyran-6-carboxamide, 1-[2-[4-[4-(aminocarbonyl)phenyl]-1-piperazinyl]ethyl]-3,4-dihydro-N-methyl-, (S)- or (1S)-1-(2-{4-[4-(aminocarbonyl)phenyl]-1-piperazinyl}ethyl)-N-methyl-3,4-dihydro-1H-isochromene-6-carboxamide, (–)-6-chloro-2-[(1-furo[2,3-c]pyridin-5-ylethyl)thio]-4-pyrimidinamine, and 6-chloro-2-{[(1S)-1-furo[2,3-c]pyridin-5-ylethyl]sulfonyl}-4-pyrimidinylamine.

3. The pharmaceutical composition of claim 1 wherein the lipophilic, pharmaceutically active agent is Irinotecan hydrochloride.

4. The pharmaceutical composition of claim 1 wherein the lipophilic, pharmaceutically active agent is in an amount of from about 1% to about 40% by weight of the total composition.

5. The pharmaceutical composition of claim 1 wherein the lipophilic, pharmaceutically active agent is in an amount of from about 5% to about 30% by weight of the total composition.

6. The pharmaceutical composition of claim 1 wherein said diglyceride is diolein, dilinoleate or a mixture thereof.

7. The pharmaceutical composition of claim 1 wherein said diglyceride is diolein.

8. The pharmaceutical composition of claim 1 wherein said monoglyceride is monoolein, monolinoleate or a mixture thereof.

9. The pharmaceutical composition of claim 1 wherein said monoglyceride is monoolein.

10. The pharmaceutical composition of claim 1 wherein the mixture of diglyceride and monoglyceride is in an amount of from about 5% to about 40% by weight of the total composition.

11. The pharmaceutical composition of claim 1 wherein the mixture of diglyceride and monoglyceride is in an amount of from about 5% to about 35% by weight of the total composition.

12. The pharmaceutical composition of claim 1 wherein the mixture of diglyceride and monoglyceride is in a ratio of about 8:2 by weight (diglyceride:monoglyceride).

13. The pharmaceutical composition of claim 1 wherein the mixture of diglyceride and monoglyceride is in a ratio of about 9:1 by weight (diglyceride:monoglyceride).

14. The pharmaceutical composition of claim 1 wherein the pharmaceutically acceptable solvent is propylene glycol.

15. The pharmaceutical composition of claim 1 wherein the pharmaceutically acceptable solvent is a mixture comprising propylene glycol and 95% (v/v) ethanol in a ratio of about 1:1.

16. The pharmaceutical composition of claim 1 wherein the pharmaceutically acceptable solvent is in an amount of from about 10% to about 30% by weight of the total composition.

17. The pharmaceutical composition of claim 1 wherein the pharmaceutically acceptable solvent is in an amount of from about 15% to about 25% by weight of the total composition.

18. The pharmaceutical composition of claim 1 wherein the pharmaceutically acceptable surfactant is Polyoxyl 40 hydrogenated castor oil or Polyoxyl 35 castor oil.

19. The pharmaceutical composition of claim 1 wherein the surfactant is in an amount of from about 10% to about 50% by weight of the total composition.

20. The pharmaceutical composition of claim 1 wherein the surfactant is in an amount of from about 30% to about 45% by weight of the total composition.

21. The pharmaceutical composition of claim 1 wherein the composition further comprises an amine.

22. The pharmaceutical composition of claim 21 wherein the amine is lower alkylamine, basic amino acid or choline hydroxide.

23. The pharmaceutical composition of claim 22 wherein the lower alkylamine is ethanolamine, diethanolamine, triethanolamine, ethylenediamine, dimethylaminoethanol or tris(hydroxymethyl)aminomethane.

24. The pharmaceutical composition of claim 22 wherein the basic amino acid is arginine, lysine or guanidine.

25. The pharmaceutical composition of claim 21 wherein the amine is in an amount from about 0.1% to about 10% by weight of the total composition.

26. A self-emulsifying formulation vehicle comprising a mixture consisting essentially of diglyceride and monoglyceride in a ratio of from about 9:1 to about 6:4 by weight (diglyceride:monoglyceride) wherein the diglyceride and monoglyceride are mono- or di- unsaturated fatty acid esters of glycerol having sixteen to twenty-two carbon chain length, one or more pharmaceutically acceptable solvents, and one or more pharmaceutically acceptable surfactants;

wherein the solvent is propylene glycol, polypropylene glycol, polyethylene glycol, glycerol, ethanol, dimethyl isosorbide, glycofurol, propylene carbonate, dimethyl acetamide, or a mixture thereof; wherein said surfactant is Polyoxyl 40 hydrogenated castor oil, Polyoxyl 35 castor oil, polyethylene glycol 12-hydroxy stearate, polyoxyethylene glyceryl trioleate, Peglicol 6-oleate, Polyoxyethylene stearates, Poloxamers, Polysorbates, or Saturated Polyglycolyzed Glycerides.

27. The self-emulsifying formulation vehicle of claim 26 further comprising an amine.

28. The self-emulsifying formulation vehicle of claim 26 wherein said diglyceride is diolein, dilinoleate or a mixture thereof.

29. The self-emulsifying formulation vehicle of claim 26 wherein said diglyceride is diolein.

30. The self-emulsifying formulation vehicle of claim 26 wherein said monoglyceride is monoolein, monoolinoleate or a mixture thereof.

31. The self-emulsifying formulation vehicle of claim 26 wherein said monoglyceride is monoolein.

32. The self-emulsifying formulation vehicle of claim 26 wherein the mixture of diglyceride and monoglyceride is in a ratio of about 7:3 by weight diglyceride:monoglyceride).

33. The self-emulsifying formulation vehicle of claim 26 wherein the mixture of diglyceride and monoglyceride is in a ratio of about 8:2 by weight (diglyceride:monoglyceride).

34. The self-emulsifying formulation vehicle of claim 26 wherein the mixture of diglyceride and monoglyceride is in a ratio of about 9:1 by weight diglyceride:monoglyceride).

35. A pharmaceutical composition according to claim 1, wherein the mixture of diglyceride and monoglyceride is prepared by mixing diglyceride and monoglyceride in appropriate relative proportion.

36. A self-emulsifying formulation vehicle according to claim 26, wherein the mixture of diglyceride and monoglyceride is prepared by mixing diglyceride and monoglyceride in appropriate relative proportion.

37. A pharmaceutical composition according to claim 1, wherein the composition is capable of forming a microemulsion upon mixing with water.

38. A pharmaceutical composition according to claim 37, wherein the microemulsion formed has an almost transparent or translucent appearance and the average particle (droplet) size of the emulsion is less than 150 nanometers (0.15 microns).

39. A pharmaceutical composition comprising:
    (a) a lipophilic, pharmaceutically active agent;
    (b) a mixture consisting of diolein and monoolein in a ratio of about 9:1 to about 8:2 by weight;
    (c) a solvent comprising propylene glycol or a mixture of propylene glycol and ethanol in an amount of from about 15% to about 25% by weight of the total composition;
    (d) a surfactant comprising glycerol polyethylene glycol oxystearate or glycerol polyethylene glycol ricinoleate in an amount of from about 30% to about 45% by weight of the total composition; and
    optionally a basic amine in an amount of about 0.1% to about 7% of the total composition; and
    wherein the lipophilic active agent has a LOG P value $\geq 2$, an intrinsic aqueous solubility $\leq 0.1$ mg/ml in the pH range of 1 to 8, and a solubility greater than 1 mg/ml in the mixture of b, c and d as defined herein.

\* \* \* \* \*